United States Patent [19]

von Bittera et al.

[11] 4,225,578
[45] Sep. 30, 1980

[54] ANIMAL COLLARS HAVING ECTOPARASITICIDAL ACTIVITY

[75] Inventors: Miklós von Bittera, Leverkusen; Hans U. Sieveking, Cologne; Wilhelm Stendel, Wuppertal; Herbert Voege, Leverkusen, all of Fed. Rep. of Germany

[73] Assignee: Bayer Aktiengesellschaft, Leverkusen, Fed. Rep. of Germany

[21] Appl. No.: 25,427

[22] Filed: Mar. 30, 1979

Related U.S. Application Data

[63] Continuation of Ser. No. 891,093, Mar. 28, 1978, abandoned.

[30] Foreign Application Priority Data

Apr. 7, 1977 [DE] Fed. Rep. of Germany ....... 2715597
Dec. 29, 1977 [DE] Fed. Rep. of Germany ....... 2758570

[51] Int. Cl.² .............. A01N 09/36; A01N 17/00; A01K 27/00; A01K 29/00
[52] U.S. Cl. ..................... 424/14; 119/106; 119/156; 424/16; 424/28
[58] Field of Search ............ 426/14, 16, 28; 119/106, 156

[56] References Cited

U.S. PATENT DOCUMENTS

| | | | |
|---|---|---|---|
| 2,205,711 | 6/1940 | Banks | 119/106 |
| 2,621,163 | 12/1952 | Coash | 424/81 |
| 2,734,483 | 2/1956 | Peo | 119/160 |
| 2,791,202 | 5/1957 | Doyle | 119/106 |
| 2,966,440 | 12/1960 | Gerolt | 424/78 |
| 3,005,747 | 10/1961 | Jacobi | 424/78 |
| 3,227,563 | 1/1966 | Fahlstrom | 106/15 |
| 3,295,246 | 1/1967 | Landsman et al. | 424/27 X |
| 3,308,022 | 3/1967 | Pauli et al. | 424/78 |
| 3,400,093 | 9/1968 | Feinberg | 260/29.6 |
| 3,852,416 | 12/1974 | Grubb et al. | 424/14 |
| 3,904,746 | 9/1975 | Aries | 424/28 |
| 3,996,348 | 12/1976 | Greenberg | 424/78 |

FOREIGN PATENT DOCUMENTS

| | | | |
|---|---|---|---|
| 2124776 | 9/1972 | France | 424/28 |
| 2237580 | 3/1975 | France | 424/28 |
| 2267045 | 11/1975 | France | 424/28 |
| 2269859 | 12/1975 | France | 424/28 |
| 2307466 | 11/1976 | France | 424/28 |
| 1444038 | 7/1976 | United Kingdom | 424/28 |

Primary Examiner—Shep K. Rose
Attorney, Agent, or Firm—Gene Harsh; Joseph C. Gil

[57] ABSTRACT

The instant invention relates to new ectoparasiticidally (especially insecticidally and acaricidally) active animal collars, which are prepared by impregnating suitable carriers with certain ectoparasiticides, and to a process for their preparation.

7 Claims, 1 Drawing Figure

ANIMAL COLLARS HAVING ECTOPARASITICIDAL ACTIVITY

This is a continuation of application Ser. No. 891,093 filed Mar. 28, 1978 now abandoned.

BACKGROUND OF THE INVENTION

Animal collars having insecticidal activity are known and are commercially available. They protect small animals, in particular dogs and cats, against infestation by Mallophaga and Siphonaptera and, in some cases, also against Ixodidae.

In general, the carriers for the collars hitherto commercially available are prepared by extruding polyvinyl chloride thermoplastics. Other natural and synthetic resins and thermoplastics have also been described as carriers for insecticides (see, for example, French Pat. No. 1,568,198), usually having O,O-dimethyldichlorovinyl phosphate (DDVP) as the insecticidal component. However, collars based on DDVP have some disadvantages, such as, for example, the occasional occurrence of skin irritation. Additionally, the collars suffer from a short life due to the high volatility of DDVP.

U.S. Pat. No. 3,852,416 describes animal collars based on polyvinyl chloride, using less highly volatile carbamates as insecticidal active compounds. Compared with these collars, animal collars according to the present invention are distinguished by an increased activity and a longer period of action.

In the following text, the vapor pressures of different ectoparasiticides are compared with one another. The vapor pressure at 20° C. is given in each case.

DDVP: $1.2 \times 10^{-2}$ mm Hg
Propoxur: $6.5 \times 10^{-6}$ mm Hg
Diazinon: $8.4 \times 10^{-5}$ mm Hg
Dimethoate: $8.5 \times 10^{-6}$ mm Hg In the case of highly volatile substances such as DDVP, the active compound passes from the collar directly into the gas phase. In the case of the less volatile substances, such as, for example, Propoxur, the active compound sublimes out of the collar and forms a white dust on the surface of the collar. Some of this passes into the vapor phase and is active there and some is distributed in the form of the dust over the animal to be treated.

Sublimation (or "efflorescence" or "exudation") of the active compound onto the collar surface has the following disadvantages:

(1) On prolonged storage, more active compound sublimes onto the surface and becomes concentrated there. When the collar is used, there is a very high dose of active compound on the surface, which ensures good immediate action but may thereby approach the point of being slightly toxic.

(2) The active compound present on the surface is rubbed off while the compound within the collar comes to the surface very slowly. Thus the release of the active compound is not linear over as long as possible a period as is desired.

(3) The crystallizing out of the active compound on the surface of the plastic coller makes the latter look extremely unattractive giving the appearance of being dusty or moldy.

BRIEF DESCRIPTION OF THE DRAWING

The drawing represents a comparison of the release times of the active compounds in collars of the instant invention when compared to those of the prior art.

DESCRIPTION OF THE INVENTION

Figure 1:
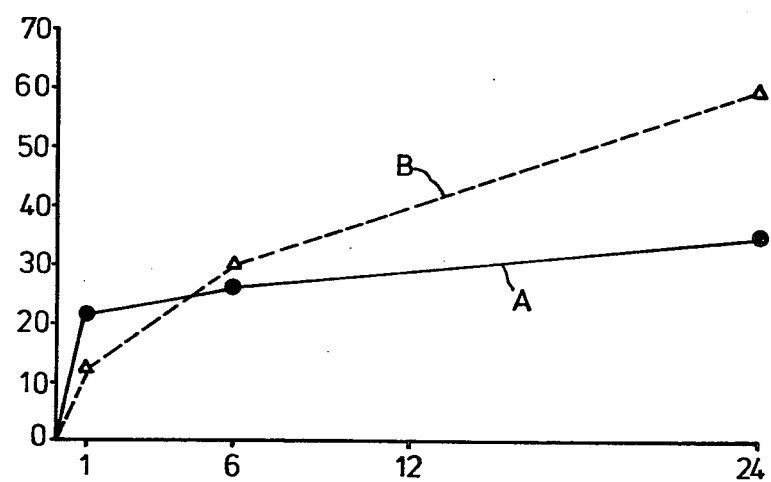

The present invention is directed to an ectoparasiticidally active animal collar containing an absorbent carrier, in which an ectoparasiticide with a vapor pressure of from $10^{-4}$ to $10^{-6}$ mm Hg at 20° C. is embedded.

The animal collars according to the invention can exhibit, inter alia, the following advantageous properties: (1) long-term action; (2) virtually linear release curve of the ectoparasiticide; (3) better stability on storage; (4) high mechanical stability; and (5) very low toxicity.

Useful absorbent carriers include, for example: natural leather and textile materials such as fleeces made of natural or synthetic fibres such as are employed for the manufacture of imitation leather. The following examples may be named: non-wovens of cotton, polyamide or polyester. The above-mentioned fleeces can be employed in the pure form or in the latex-treated form. Fleeces consisting of natural hair can also optionally be used, as can fluffy fabrics with good absorbency. Examples of non-wovens which may be used according to the present invention are disclosed in U.S. Pat. No. 3,985,929, herein incorporated by reference.

The carrier is impregnated with a solution of the ectoparasiticidal active compound in a suitable solvent and the solvent is removed (in general it is merely evaporated off). One or both surfaces may then optionally be after-treated.

The solvents employed must have the following properties: (a) the ectoparasiticide must be soluble therein; (b) the solvent must be able to wet the carrier; (c) evaporation of the solvent must be possible without essential evaporation of the ectoparasiticide; and (d) the solvent must be inert towards the carrier.

Preferred solvents include alcohols, such as methanol, ethanol or isopropanol; ketones, such as acetone; ethylene glycol ethers, such as ethylene glycol monomethyl ether; or halogenated hydrocarbons, such as methylene chloride or chloroform.

Preferred ectoparasiticides with a vapor pressure of from $10^{-4}$ to $10^{-6}$ mm Hg at 20° C. are known and are selected from the carbamate and phosphoric acid ester classes of substances. Propoxur (2-isopropoxyphenyl N-methylcarbamate) is especially preferred as the active compound. Compounds of this type are known and are described, for example, in U.S. Pat. No. 3,852,416, the disclosure of which is herein incorporated by reference. Their preparation is described in U.S. Pat. Nos. 2,903,478 and 3,203,853, both disclosures of which are herein incorporated by reference.

Examples of other carbamates which are suitable include 3-tolyl-N-methylcarbamate, 3,4-xylyl-N-metyl carbamate, m-(1-methylbutyl)-phenyl-N-methylcarbamate, (2-etylthiomethyl-phenyl)-N-methylcarbamate, 4-dimethylamino-m-tolyl-N-methylcarbamate, 2,3-dihydro-2,2-dimethylbenzfuran-7-yl-N-methylcarbamate, 2-dimethylcarbamoyl-3-methyl-5-pyrazolyl-dimethylcarbamate, 2-dimethylamino-5,6-dimethyl-pyrimidin-4-yl-dimethylcarbamate, and the like.

If a rapid release is desired, the flesh side of the leather or the appropriate side of the fleece remains open. If the release is to be retarded an after-treatment is carried out. In this case, preferably, a thin coating of a conventional leather finish such as, for example, an aqueous dispersion of an acrylic resin, PVC or polyurethane, is sprayed onto the appropriate side, or casein is optionally applied. In general, one surface of the leather or fleece may be coated with a conventional leather varnish, for example one based on polyurethane, PVC or acrylic resin. An elegant finish can be thereby achieved. Examples for casein based finishes are disclosed in U.S. Pat. No. 3,943,252 herein incorporated by reference.

The collar can be given a pleasing exterior by adhering to the treated carrier a textile, imitation leather, split leather or a film.

In a preferred embodiment of the invention natural leather or synthetic leather which possibly can already be finished on the outside but which are at least not yet finished on the flesh side are used as absorbent carriers, whereby the leather is impregnated for instance by casting a solution by containing the ectoparasiticide onto the flesh side of the leather or applying any other convenient method of impregnation, freeing it from the solvent in which the ectoparasiticide is dissolved, for example by an evaporation process and then finishing the unfinished surface(s) of the leather with a leather finish, for example by spraying a polyurethane leather finish onto the surface of the leather or by using any other convenient method for finishing leather. The finished leather can then be cut into animal collars and can be provided with buckles.

In the preparation of the animal collars having ectoparasiticidal activity, the absorbent carrier is impregnated e.g. by dipping, pouring or spraying with a solution of the ectoparasiticidal active compound in which the dissolved amount of ectoparasiticidal active compound is at least 2 percent, preferably at least 5 percent by weight, based on the weight of the absorbent carrier. The absorbent carrier then absorbs the total amount of active compound and the solvent for ectoparasiticide is subsequently removed, for example by evaporation.

The animal collars according to the present invention are preferably used for livestock and/or pets; cattle, dogs and cats may be mentioned in particular.

The animal collars according to the present invention may be successfully employed against numerous harmful animal parasites (ectoparasites) from the class of Arachnidae and the class of insects.

Examples of ecotoparasites of the class of Arachnidae, which figure prominently in tropical, subtropical and temperate latitudes, include from the family of Ixodidae, the Australian and South American one-host cattle tick (*Boophilus microplus*), the African one-host cattle tick (*Boophilus decoloratus*) and multi-host ticks which are parasitic on livestock and pets in all continents, such as *Rhipicephalus appendiculatus, Rhipicephalus evertsi, Amblyomma variegatum, Amblyomma hebraeum, Amblyomma cayennense, Hyalomma truncatum, Dermacentor variabilis* and *Ixodes ricinus*, as well as, from the family of Gamasidae, the red poultry mite (*Dermanyssus gallinae*).

Examples of ectoparasites of the class of insects include: Mallophaga, for example the dog biting louse (*Trichodectes canis*), the cattle biting louse (*Damalinea bovis*), the sheep biting louse (*Damalinea ovis*) and the poultry biting louse (*Eomenacanthus stramineus*); Anoplura, for example the cattle louse (*Haematopinus eurysternus*) and the pig louse (*Haematopinus suis*); Diptera, for example the sheep ked (*Melophagus ovinus*); and Aphaniptera, for example the dog flea (*Ctenocephalides canis*).

The invention is further illustrated, but is not intended to be limited by the following examples in which all parts and percentages are by weight unless otherwise specified.

EXAMPLES

EXAMPLE 1

(a) Leather 2.5 mm thick and without surface treatment was weighed.

(b) An amount of Propoxur equivalent to 1/10 that of the weight of the leather was weighed out and dissolved in an amount of methanol equivalent to 2/10 of the weight of the leather.

(c) The leather was uniformly impregnated by casting the solution onto the flesh side.

(d) The leather was freed from solvent by drying (at 50° C. to constant weight).

(e) The surface was dressed with a polyurethane leather finish by spraying it onto the surface (polyurethane finish used: BAYGEN ® TOP U).

(f) The finished leather was cut into animal collars and provided with buckles.

EXAMPLE 2

The procedure was analogous to Example 1, but a fleece having a thickness of 5 mm such as is employed in the manufacture of imitation leather was used instead of leather. The fleece applied consisted of 70 percent of polycaprolactame and 30 percent of polyester Trevira ®.

EXAMPLE 3

The process steps (a) to (d) were carried out in a manner similar to Exmple 1. Further processing took place as follows:

(e) 125 ml per m² of a 30 to 40% strength aqueous acrylate dispersion (EUDERM ® 25 A) were sprayed onto the flesh side and the water was dried off.

(f) The surface was dressed with leather varnish in accordance with the method of Example 1.

(g) The material thus finished was cut into dog collars and provided with buckles.

EXAMPLE 4

The procedure was similar to Example 3, with the difference that a fleece as disclosed in Example 2 was employed instead of the leather.

EXAMPLE 5

(a) Leather 2.3 mm thick and without surface treatment was weighed.

(b) An amount of Propoxur equivalent to 1/20 that of the weight of the leather was weighed out and dissolved in an amount of ethanol equivalent to 1/10 of the weight of the leather.

(c) The leather was uniformly impregnated by casting the solution to the flesh side.

(d) The leather was freed from solvent by drying (at 70° C. to constant weight).

(e) The finished leather was cut into animal collars and provided with buckles.

EXAMPLE 6

The procedure was similar to Example 3, with the difference that the fleece of Example 2 was used instead of leather and that in process step (b) an amount of Propoxur which corresponded to 1/20 of the weight of the imitation leather fleece was weighed out.

EXAMPLE A

Release model for Propoxur dog collars

I. Principle

The release of Propoxur from dog collars in water was followed in a rotary flask apparatus over a period of 24 hours. The content of active compound in the release medium was determined colorimetrically, after hydrolysis to isopropoxyphenol, and the content of Propoxur in the collar was determined by thin layer chromatography, after Soxhlet extraction. The percentage release was obtained by relating the absolute amount of active compound released up to time (t) to the content of active compound in the collar in the portion weighed (x).

II. Release conditions 2 g of dog collar (in one piece) and 200 ml of distilled water were put into each vessel of a Souder and Ellenbogen rotary flask apparatus. The release was effected at 37° C. and at 25 revolutions/minute. Samples of 2 ml each were taken at the start and after 1, 6 and 24 hours.

III. Determination of the Propoxur content in the release medium (colorimetry)

For each sample, 2 ml of 2 N sodium hydroxide solution were added, the mixture was left to stand for 30 minutes, 2.5 ml of 2 N hydrochloric acid were added and the color reaction was carried out with 4-nitrobenzenediazonium tetrafluoborate. The maximum extinction at 508 nm was measured.

Determination of Propoxur in dog collars

This was effected by thin layer chromatography and UV spectroscopic analysis.

Comparison solution 100 mg of Propoxur were dissolved in 50.0 ml of methanol.

Test solution (a) PVC collars 1 g of ground collar was boiled with about 30 ml of tetrahydrofuran (THF) under reflux until it had completely dissolved (about 1 hour). After cooling, the mixture was diluted with THF to 50 ml.

(b) Leather collars and imitation leather collars 4 g of the ground collar (pieces 1 mm) were extracted with about 150 ml of methanol in a Soxhlet apparatus for 2 hours. After cooling, the mixture was diluted with methanol to 200 ml.

Procedure 250 ml each of the test solution and comparison solution were applied 6 cm apart to silica gel finished plates (F 254 Merck, Darmstadt) and chromatographed over 15 cm with chloroform/ethyl acetate (60/40) under chamber saturation. The separated spots were marked under UV light (254 nm) and eluted with 2 ml of methanol; the UV spectrum of the eluates was determined at 270 nm.

The laboratory release of Propoxur from a PVC dog collar and from a leather collar (prepared by impregnation, according to Example 1 above) can be seen from FIG. 1.

In FIG. 1, the ordinate gives the release of active compound in percent, while the abscissa gives the number of hours (measuring time).

The individual curves in FIG. 1 relate to the following collars:

Curve A: Propoxur/PVC collar.

Curve B: Propoxur collar according to Example 1.

What is claimed is:

1. A process for the preparation of an animal collar comprising impregnating an absorbent carrier selected from the group consisting of natural leather and synthetic leather with a solution of 2-isopropoxyphenyl N-methylcarbamate, thereafter removing the solvent and optionally, after-treating one or both surfaces.

2. A process according to claim 1 in which one or both surfaces of the carrier are varnished after removal of the solvent.

3. A process according to claim 2 in which the varnish is a leather varnish based on acrylic resin, polyvinyl chloride or polyurethane.

4. A process according to claim 2, in which the solvent used is selected from the group consisting of alcohols, ketones, ethylene glycol ethers or halogenated hydrocarbons.

5. A process according to claim 4, in which the solvent is an alcohol selected from the group consisting of methanol, ethanol or isopropanol.

6. An animal collar obtained according to the process of claim 1.

7. A method of protecting or freeing an animal from ectoparasites which comprises fitting the animal with a collar comprising an absorbent carrier selected from the group consisting of natural leather and synthetic leather, said collar being impregnated with a solution of 2-isopropoxyphenyl N-methylcarbamate after which the solvent has been removed and, optionally, said collar having one or both surfaces after-treated.

* * * * *